United States Patent [19]

Li

[11] Patent Number: 5,567,831
[45] Date of Patent: Oct. 22, 1996

[54] NON-STEROIDAL SULFATASE INHIBITOR COMPOUNDS AND THEIR METHOD OF USE

[75] Inventor: Pui-Kai Li, Library, Pa.

[73] Assignee: Duquesne University of the Holy Ghost, Pittsburgh, Pa.

[21] Appl. No.: 516,021

[22] Filed: Aug. 16, 1995

[51] Int. Cl.$^6$ .................. A61K 31/16; A61K 31/165; A61K 31/185
[52] U.S. Cl. .................. 554/43; 514/579; 514/600; 514/601; 514/608; 514/625; 514/630; 558/50
[58] Field of Search .................. 554/43; 558/50; 514/579, 601, 600, 608, 625, 630

[56] References Cited

U.S. PATENT DOCUMENTS 5,510,379  4/1996  Lee et al. ........................ 558/50

OTHER PUBLICATIONS

Lowry, O. H. et al., "Protein Measurement With The Folin Phenol Reagent", *J. Biol. Chem.*, pp. 265–275 (1951).
Millington, D. S., "Determination Of Hormonal Steroid Concentrations In Biological Extracts By High Resolution Mass Fragmentograph", *Journal Of Steroid Biochemistry*, vol. 6, pp. 239–245 (1975).
Reed, K. C. et al., "Kinetic Properties Of Human Placental Aromatase", *Journal Of Biological Chemistry*, vol. 251, No 6, pp. 1625–1631 (Mar. 25, 1976).
Santner, S. J. et al., "In Situ Estrogen Production Via The Estrone Sulfatase Pathway in Breast Tumors: Relative Importance versus The Aromatase Pathway", *Journal of Clinical Endocrinology and Metabolism*, vol. 59, No. 1, pp. 29–33 (1984).
Santen, R. J. et al., "Enzymatic Control Of Estrogen Production In Human Breast Cancer: Relative Significance Of Aromatase versus Sulfatase Pathways", *Annals New York Academy Of Sciences*, vol. 464, pp. 126–137 (1986).
Duncan, L. et al., "Inhibition Of Estrone Sulfatase Activity By Estrone-3-Methylthiophosphonate: A Potential Therapeutic Agent In Breast Cancer", *Cancer Research*, vol. 53, pp. 298–302 (1993).
Howarth, N. M. et al., "Phosphonates And Thiophosphonates As Sulfate Surrogates: Synthesis Of Estrone 3-Methylthiophosphonate, A Potent Inhibitor Of Estrone Sulfatase", *Bioorganic & Medical Chemistry Letters*, vol. 3, No. 2, pp. 313–318 (1993).
Li, Pui-Kai et al., "Synthesis And Biochemical Studies Of Estrone Sulfatase Inhibitors", *Steroids*, vol. 58, pp. 106–111 (Mar. 1993).
Dibbelt, L. et al., "Inhibition Of Human Placental Sterylsulfatase By Synthetic Analogs Of Estrone Sulfate", *J. Steroid Biochem. Molec. Biol.*, vol. 50, No. 5/6, pp. 261–266 (1994).
Howarth, N. M. et al., "Estrone Sulfamates: Potent Inhibitors Of Estrone Sulfatase With Therapeutic Potential", *J. Med. Chem.*, vol. 37, pp. 219–221 (1994).
Registry of Toxic Effects of Chemical Substances, N.I.O.S.H. RTECS Number UE5093500 (1979) from U.S. Army Armament Research and Development Command, Chemical Systems Laboratory.

*Primary Examiner*—Peter O'Sullivan
*Attorney, Agent, or Firm*—Arnold B. Silverman; Jolene W. Appleman; Eckert Seamans Cherin & Mellott

[57] ABSTRACT

This invention discloses compounds useful as non-steroidal sulfatase inhibitors. The compounds comprise the formula (1)

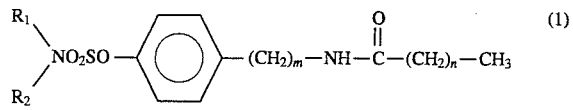

wherein (a) $R_1$ is selected from the group consisting of hydrogen and a lower alkyl group, (b) $R_2$ is selected from the group consisting of H and a lower alkyl group, (c) m is an integer from 0 to 4, and (d) n is an integer from 5 to 14. $R_1$ is selected from the group consisting of H and $C_1$–$C_6$ alkyl and $R_2$ is selected from the group consisting of H and $C_1$–$C_6$ alkyl. The invention also discloses methods of treating a patient prophylactically to provide protection as an estrogen depleting agent for estrogen dependent illnesses and treating a patient therapeutically for estrogen dependent diseases. A method of making the non-steroidal sulfatase inhibitors is also disclosed.

20 Claims, 5 Drawing Sheets

NON-STEROIDAL SULFATASE INHIBITOR COMPOUNDS AND THEIR METHOD OF USE

BACKGROUND OF THE INVENTION

1. Field of the Invention

This invention relates to (p-o-sulfamoyl)-N-alkanoyl p-hydroxy phenylamine compounds. More specifically, it relates to non-steroidal compounds useful as steroid sulfatase inhibitors in estrogen dependent illnesses. Methods of employing these compounds for therapeutic and prophylactic treatment are also provided.

2. Background Information

Estrogen levels in breast tumors of post-menopausal women are at least ten times higher than estrogen levels in plasma. [Millington, "Determination of hormonal steroid concentrations in biological extracts by high resolution fragmentography", *J. Steroid Biochem.*, Vol. 6, pp. 239–245 (1975).] The high levels of estrogen in these tumors is due to in situ formation of estrogen, possibly through conversion of estrone sulfate to estrone by the enzyme estrone sulfatase. [Santner et al., "In situ estrogen production via the estrone sulfatase pathway in breast tumors: Relative importance versus the aromatase pathway, *J. Clin. Endocrinol Metab.*, Vol. 59, pp. 29–33 (1984); Santen et al., "Enzymatic control of estrogen production in human breast cancer: Relative significance of aromatase versus sulfatase pathways", *Ann. N. Y. Acad. Sci.*, Vol. 464, pp. 126–137 (1986).] Therefore, inhibitors of estrone sulfatase are potential agents for the treatment of hormone-dependent breast cancer. Most estrone sulfatase inhibitors are estrone derivatives. Reed and his co-workers reported on the sulfatase inhibitory activities of estrone-3-0-methylthiophosphonate, estrone 3-0-alkyl and aryl sulfonates, estrone-3-0 phosphonates and thiophosphonates and estrone sulfamates on MCF-7 cells and in human placental microsomes and breast tumor preparations. [Duncan et al., "Inhibition of estrone sulfatase activity by estrone 3-methylthiophosphonate", *Cancer Res.*, Vol. 53, pp. 298–303 (1993); Howarth et al., "Phosphonates and thiophosphonates as sulfate surrogates: Synthesis of estrone-3-methylthiophosphonate, a potent inhibitor of estrone sulfatase", *Bioorg. Med. Chem. Lett.*, Vol. 3, pp. 313–318 (1993); Howarth et al., "Estrone Sulfamates: Potent inhibitors of estrone sulfatase with therapeutic potential", *J. Med. Chem.*, Vol. 37, pp. 219–221 (1994).] From studying the synthesis and sulfatase binding affinity studies of estrone phosphate, desoxyestrone-3-methylene sulfonate, it was hypothesized that an oxygen atom or at least a sterically or electronically similar link between the steroid ring and the sulfonate moiety is essential for high affinity binding to the sulfatase. [Li et al., "Synthesis and biochemical studies of estrone sulfatase inhibitors", *Steroids*, Vol. 58, pp. 106–111 (1993); Dibbelt et al., "Inhibition of human placental sterylsulfatase by synthetic analogs of estrone sulfate", *J. Steroid Biochem. Molec. Biol.*, Vol. 50, Nos. 5/6, pp. 261–266 (1994)]. Of all the reported estrone sulfatase inhibitors in the literature, estrone 3-0 sulfamate is the most potent inhibitor. However, in uterine weight gain assay in rats, estrone 3-0 sulfamate and its analogues is estrogenic (unpublished result) and, therefore, is not useful in the treatment of hormone-dependent breast cancer.

Therefore, in spite of the prior art disclosures, there remains a very real and substantial need for a non-steroidal estrone sulfatase inhibitor that is more metabolically stable, more active and more selective than other known sulfatase inhibitors. There is also a need for these non-steroidal estrone sulfatase inhibitors to have antitumor activity or act as synergistic agents with antiestrogen and aromatase inhibitors and for methods of using these compounds.

SUMMARY OF THE INVENTION

The present invention has met the hereinbefore described need. The present invention provides compounds comprising the formula (1)

wherein (a) $R_1$ is selected from the group consisting of hydrogen and $C_1$–$C_6$ alkyl, (b) $R_2$ is selected from the group consisting of H and $C_1$–$C_6$ alkyl, (c) m is an integer from 0 to 4 and (d) n is an integer from 5 to 14. $C_1$–$C_6$ alkyl can be branched or unbranched.

This invention provides a process of using the derivatives of (p-o-sulfamoyl)-N-alkanoyl p-hydroxyphenylamine which are non-steroidal estrone sulfatase inhibitors of formula (1) described above for therapeutic and prophylactic purposes including employing these compounds as antitumor agents and as synergistic agents with antiestrogen and aromatase inhibitors. (p-o-sulfamoyl)-N-alkanoyl p-hydroxyphenylamine compounds of this invention substantially inhibit steroid sulfatase compounds. This invention provides a process of using the (p-o-sulfamoyl)-N-alkanoyl p-hydroxyphenylamine compounds for therapeutic and prophylactic purposes as antitumor and synergistic agents against estrogen dependent illness selected from the group consisting of breast cancer, endometrial cancer, vaginal cancer, ovarian cancer and endometriosis.

It is an object of this invention to provide compounds for substantially inhibiting the steroid sulfatase enzyme produced in the body.

It is an object of this invention to provide non-steroidal estrone sulfatase inhibitor compounds having antitumor or synergistic activity with antiestrogen and aromatase inhibitors.

It is a further object of this invention to provide non-steroidal estrone sulfatase inhibitor compounds providing effective activity against estrogen dependent diseases such as, for example, breast cancer, ovarian cancer, vaginal cancer, endometrial cancer and endometriosis.

It is a further object of this invention to provide a method of using in a patient a therapeutically effective dosage of non-steroidal estrone sulfatase inhibitor compounds.

It is another object of this invention to provide a method of using in a patient a prophylactically effective dosage of the non-steroidal estrone sulfatase inhibitor compounds as an estrogen depleting compound for women at risk.

It is yet another object of this invention to provide derivatives of non-steroidal estrone sulfatase inhibitor compounds that are not metabolized to compounds that are estrogenic.

DESCRIPTION OF THE PREFERRED EMBODIMENT

As used herein, the term "patient" is limited to human beings.

Estrogen levels in breast tumors of post-menopausal women are as much as ten times higher than estrogen levels in plasma. The high level of estrogen in these tumors is postulated to be due to in situ formation of estrogen. Estrone sulfate is the most abundant circulating estrogen in women and the enzyme estrone sulfatase has been shown to be present in breast cancer cells. Furthermore, estrone sulfate has been shown to stimulate growth of nitrosomethyl urea-induced tumor cells in castrated rats. Thus, inhibitors of estrone sulfatase are potential agents for treatment of estrogen dependent diseases such as breast cancer, ovarian cancer, vaginal cancer, endometrial cancer and endometriosis.

The compounds comprise the formula (1)

wherein $R_1$ is selected from the group consisting of hydrogen and a lower alkyl group and $R_2$ is selected from the group consisting of H and a lower alkyl group and m is an integer from 0 to 4 and n is an integer from 5 to 14. The lower alkyl group has 1 to 6 carbons, branched and unbranched. Most preferably $R_1$ is H and $R_2$ is H, n is 11 and m is 2. Preferably, $R_1$ is H and $R_2$ is H, n is 10 and m is 2. Preferably, $R_1$ is H and $R_2$ is H, n is 13 and m is 0.

In this invention the method of therapeutically treating a patient for an estrogen dependent illness comprises providing a compound of formula (1)

given hereinabove, incorporating the compounds in a suitable pharmaceutical carrier, administering a therapeutically effective dosage of the compound incorporated in the carrier to a patient, and employing the method in therapeutically treating a patient for an estrogen dependent illness selected from the group consisting of breast cancer, vaginal cancer, endometrial cancer, ovarian cancer and endometriosis.

The method also includes prophylactically administering to a patient comprising providing a compound of formula (1), incorporating the compound in a suitable pharmaceutical carrier, administering a prophylactically effective dosage of the compound incorporated in the carrier to a patient and employing the method in prophylactically administering to a patient at risk an estrogen depleting compound to provide protection against estrogen dependent diseases selected from the group consisting of breast cancer, vaginal cancer, endometrial cancer, ovarian cancer and endometriosis.

Examples of suitable pharmaceutical carriers are physiologic saline (0.9% sodium chloride) 95% dextrose in water.

The compounds of this invention incorporated into the pharmaceutical carrier may be administered to a patient by parenteral injection, such as for example, intravenously, intrathecally, intramuscularly or intra-arterially. Other potential routes of administration include, for example, orally, transdermally or by other means. The dosage of, route of, administration of and duration of therapy with the compounds of this invention, which can be readily determined by those skilled in the art, will be individualized according to the estrogen dependent illness being treated, body weight of the patient, other therapy employed in conjunction with the compounds of this invention and the condition, clinical response and tolerance of the patient. The typical patient will be a postmenopausal female or premenopausal female who has been ovariectomized.

A method for preparing the compounds comprising the formula (1)

wherein $R_1$ is selected from the group consisting of hydrogen and a lower alkyl group, $R_2$ is selected from the group consisting of H and a lower alkyl group, m is an integer from 0 to 4 and n is an integer from 5 to 14, the method comprises adding alkanoyl chloride dropwise into a cooled solution of p-hydroxyphenylamine and triethyl amine to form a first mixture. The first mixture is then extracted to give a first product N-alkanoyl-p-hydroxyphenylamine. A hydride and a sulfamide are added to said first product to form a second mixture. The second mixture is then extracted to give a second product (p-o-sulfamoyl)-N-alkanoyl p-hydroxyphenylamine.

Figure 1:
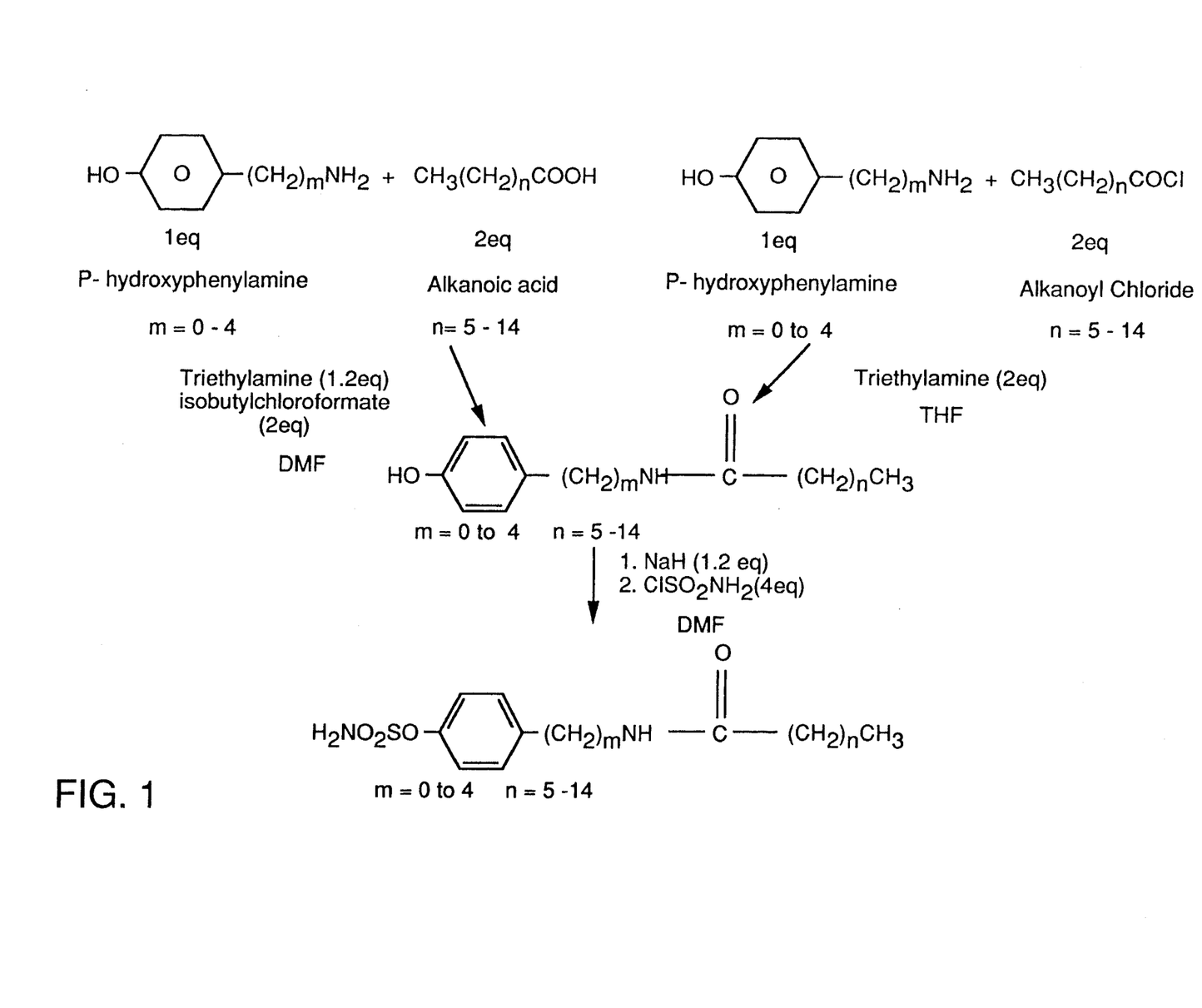
FIG. 1 discloses the synthesis of the non-steroidal sulfatase inhibitors of the present invention.

The following is an example as shown in FIG. 1 of how a preferred compound was prepared and tested. Examples are given hereinbelow.

EXAMPLE I

The synthesis of N-nonanoyl tyramine was as follows:

Procedure—Nonanoyl chloride (2.74 m, 14.6 mmol) was added dropwise to a cooled solution of tyramine (1 g, 7.29 mmol) and triethylamine (2.03 ml, 14.6 mmol) in THF (35 ml). The reaction mixture was stirred at room temperature for 48 hours. It was then poured into 10% HCl solution (70 ml) and the mixture was then extracted with ethyl acetate (3×50 ml). The ethyl acetate layer was separated, dried (MgSO$_4$) and concentrated under reduced pressure to give crude N-nonanoyl tyramine. The product was purified by chromatography on a silica gel column eluted with methylene chloride/ethyl acetate (30:1). m.p. 65.9° to 66.7° C. IR (KBr) 3306, 2922, 2851, 1638; $^1$H NMR δ 6.65–6.98 (d of d, 4 H, aromatic), 7.78 (t, 1 H, NH), 9.15 (s, 1 H, OH). Analysis calculated for $C_{17}H_{27}NO_2$: C, 73.61; H, 9.81; N, 5.05. Found C, 73.49; H, 9.661; N, 5.31.

EXAMPLE II

The synthesis of (p-o-sulfamoyl)-N-nonanoyl tyramine was as follows:

Procedure—In a stirred solution of N-nonanoyl tyramine (1 g, 3.6 mmol) in anhydrous DMF (20 ml) at 0° C. under nitrogen was added sodium hydride (173 mg, 7.2 mmol). The solution was stirred for 30 minutes and chlorosulfonamide (832 mg, 14.4 mmol) was added in one portion. The solution was then stirred at room temperature for 24 hours. The mixture was poured into a cold saturated sodium bicarbonate solution and the resulting solution was extracted with methylene chloride (3×50 ml). The organic layer was separated, dried (MgSO$_4$) and concentrated under reduced pressure to give a light yellow solid. The product was purified by chromatography on a silica gel column eluted with methylene chloride/ethyl acetate (20:1). m.p. 104.3°–104.5° C. IR (KBr) 3383, 3290, 2918, 1686 cm$^{-1}$; $^1$NMR δ 7.17–7.29 (d of d, 4 H, aromatic). 7.87 (t, 1H, NH). 7.94 (S, 2H, SO$_2$NH$_2$). Analysis calculated from C$_{17}$H$_{28}$N$_2$O$_4$S: c, 57.28; H, 7.92; N, 7.86. Found C, 57.37; H, 8.01; N, 7.63.

The methods of testing the prepared compounds were as follows:

EXAMPLE III

Preparation of Human Placental Microsome

Human placenta were obtained immediately upon delivery from Mercy Hospital of Pittsburgh, Pa. and stored on ice during transportation to the laboratory. The preparation of microsomes was performed according to the method of Reed and Ohno [Reed et al, *J. Bio. Chem.*, 251, 1625 (1976)]. All procedures were carried out at 0°–4° C. The placenta was cut free of connective tissue and large blood vessels with scissors. The tissue was then homogenized in a waring blender with two parts of tissues to one part of homogenization buffer consisting of 0.05M sodium phosphate, 0.25M sucrose, and 0.04M nicotinamide, pH 7. The homogenate was centrifuged at 10,000 g for 30 minutes. The debris was discarded and the supernatant was centrifuged at 105,000 for one hour. The procedure was repeated once again and the resulting pellets were stored at −80° C. until assayed. The pellets were used within six weeks after preparation.

Protein concentrations were determined according to Lowry [Lowry et al., *J. Biol. Chem.*, 193, 265 (1951)].

Stock solution of estrone sulfate substrate E1S was prepared in 0.1 m Trisacetate, pH 7.0. All the inhibitors were dissolved prior to the experiments in ethanol. Estrone sulfatase activity was assayed radiometrically using [6,7-$^3$H] E1S. The radioactive substrate was used as a tracer for the enzyme reaction.

EXAMPLE IV

Inhibitors' Screening Assay Procedure

The final volume of the enzyme assay was 1'ml. [6,7-$^3$H] estrone sulfate (20 μM/tube; 300,000 dpm/tube) in ethanol and an inhibitor at various concentrations in ethanol were added to a 5 ml test tube. The ethanol was removed with a stream of nitrogen. Tris-HCl buffer (0.05 m, pH 7.2, 0.2 ml) was added to each tube. The placental microsomes were then diluted with 0.05 m Tris-HCl buffer pH 7.2 to a concentration of 300 ug/ml. The microsomes and assay tubes containing inhibitors were preincubated for 5 minutes at 37° C. in a water bath shaker.

The assay began by the addition of the substrate estrone sulfate. After 20 minutes of incubation at 37° C., 4 ml of toluene were added to quench the assay. [$^{14C}$]Estrone (10,000 dpm/tube) were added concurrently with the toluene as an internal standard for the determination of extraction efficiency. Control sample with no inhibitor were incubated simultaneously. Blank samples were obtained by incubating boiled microsomes. The quenched samples were vortexed for 45 seconds and centrifuged (2,000 rpm for 10 minutes). On milliliter of toluene was obtained from each quenched sample to determine the amount of product formation. Cell samples were run two times in triplicate with a variation of less than about 7%. Product formation for samples containing an inhibitor was compared to that of control samples (without inhibitors) run simultaneously. This was reported as percent inhibition of control sample which equals $$100\% \times \frac{\text{product formation for sample containing inhibitor}}{\text{product formation for sample with no inhibitor (control)}}$$

EXAMPLE V

Determination of IC$_{50}$ Values

Figure 2A:
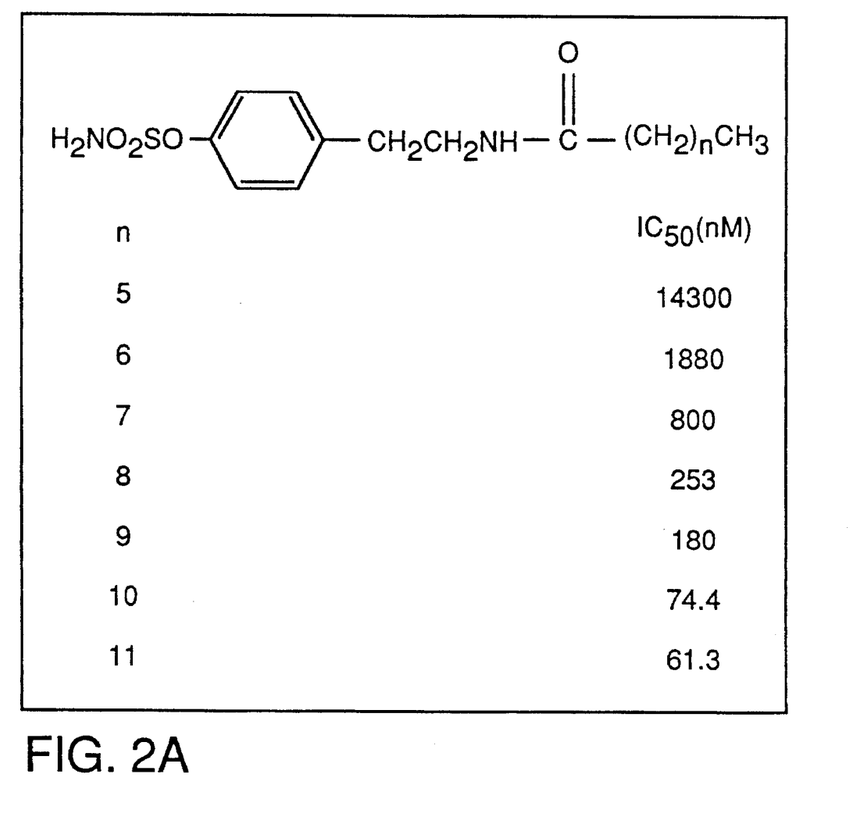
FIG. 2a discloses a table of the inhibitory effect of non-steroidal sulfatase inhibitors (m=2, n=5–11).
Figure 2B:
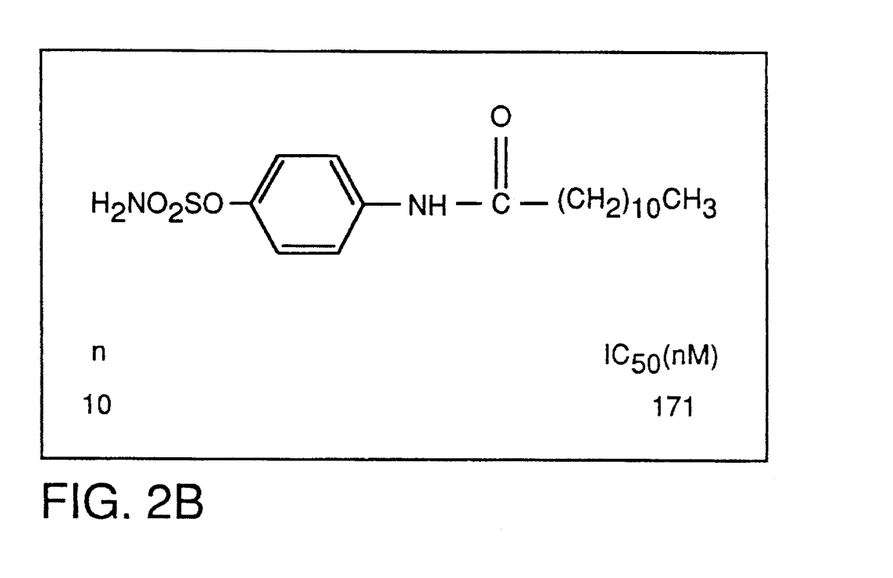
FIG. 2b discloses a table of the inhibitory effect of non-steroidal sulfatase inhibitors where m=0 and n=10.

The estrone sulfatase inhibitory activity of the synthesized inhibitors were tested using human placental microsomes as the enzyme source since they contain high amounts of estrone sulfatase activity. To determine the relative potency of the inhibitors to inhibit human placental microsomal estrone sulfatase activity, the activity in the presence of increasing amounts of inhibitor concentration was determined. For these experiments, a microsomal protein concentration of 250 μg/ml was used. The proteins (containing estrone sulfatase) were incubated with various concentrations of inhibitor. The concentration of the inhibitor to achieve 50% inhibition of estrone sulfatase activity in the microsome (when compared with the control with no inhibitor) was given a value called IC$_{50}$ value in nanomolar concentration. The smaller the IC$_{50}$ value, the more potent the inhibitor is. This is shown in FIG. 2*a* m=2 and n=5–11, where a table of the inhibitory effect of non-steroidal sulfatase inhibitors to estrone sulfatase from human placental microsome, utilizing estrone sulfate (20 μm) as the substrate is shown. Each value represents the mean of two determinations in triplicate (variability <7% ). FIG. 2*b* shows the same calculation where m=0 and n=10.

EXAMPLE VI

In Vitro Estrogen Sulfatase Assay on Cell Monolayers

Figure 3:
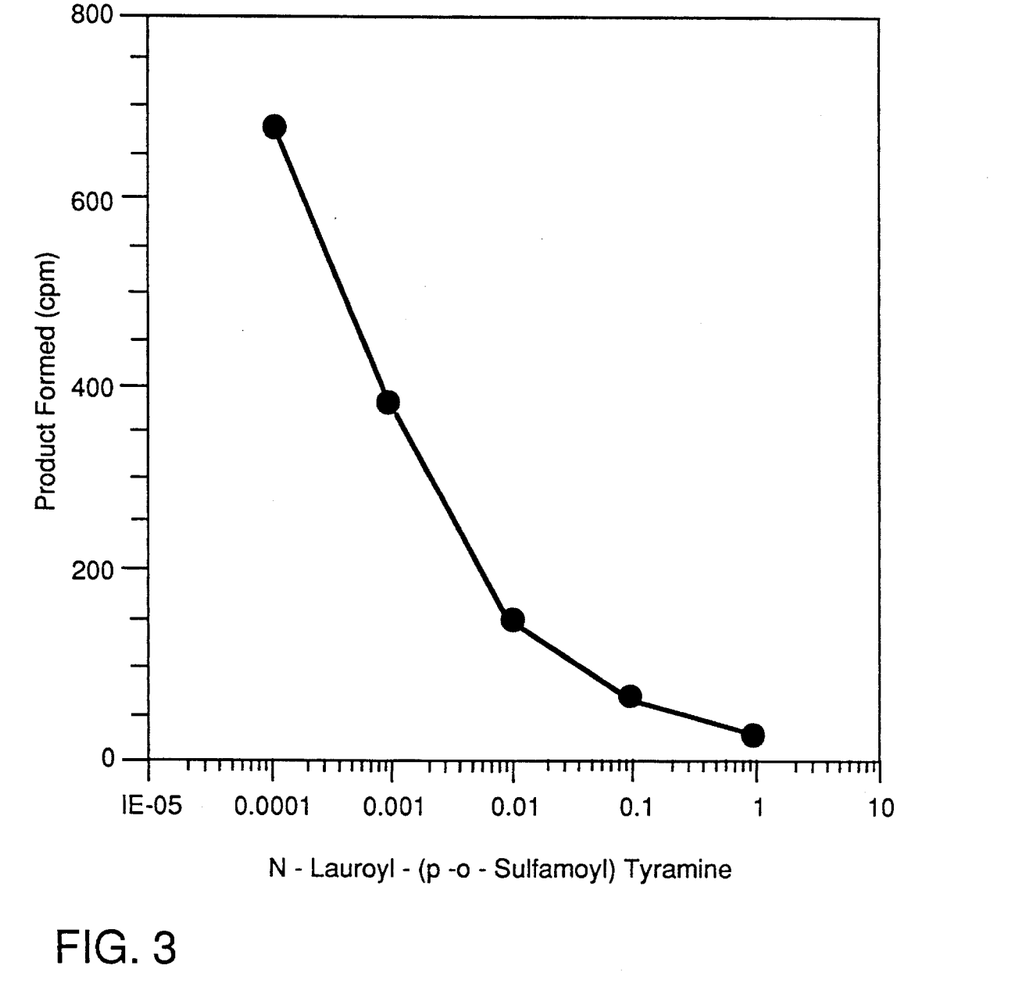
FIG. 3 discloses concentration-dependent inhibition of estrone sulfatase activity in intact MDA-MB-231 breast cancer cells for the non-steroidal compounds where m=2 and n=10.

The in vitro sulfatase assay on intact cells involved a modification of the procedure of Duncan et al. ["Inhibition of estrone sulfatase activity by estrone 3-methylthiophosphonate", *Cancer Res.*, Vol. 53, pp. 298–303 (1993)]. Intact nearly confluent monolayers of MDA-MB-231 (American Type Culture Collection) breast cancer cells in 6-well tissue-culture plates were washed with Hank's balanced salt solution (HBSS) and incubated for 18 hours at 37° C. with [$^3$H]E$_1$S (5 pmol, 7×10$^5$ dpm) in serum-free Minimal Essen- tial Medium (MEM) (2.5 ml) with or without test compounds (0.01 nM to 10 μM). After incubation, each dish was cooled and aliquots of the medium (0.5 ml) were pipetted into separate tubes containing 3 ml toluene. The mixture was shaken vigorously for 30 seconds and then centrifuged for 3 minutes at 2500 x g. Previous experiments have shown that >90% of estrone ($E_1$) and <0.1% of estrone sulfatase ($E_1S$) is removed from the aqueous phase by this treatment. Aliquots (1 ml) of the organic phase were removed and added to 5 ml scintillation cocktail (Omnifluor, ICN). Radioactivity was determined using a Packard TriCarb scintillation counter with 50% efficiency for $^3H$. Each batch of experiments included dishes without cells (to assess apparent non-enzymatic hydrolysis of the substrate). All treatments were run in duplicate, with extractions performed in triplicate for each treatment. FIG. 3 shows the concentration-dependent inhibition of estrone sulfatase activity in intact MDA-MB-231 breast cancer cells. Monolayers of MDA-MB-231 cells (human breast cancer cells containing high activity of estrone sulfatase) in 6-well plates were incubated for 18 hours at 37° C. with [$^3H$]$E_1S$ (2 nM) and the non-steroidal compound N-lauroyl-(p-o-sulfamoyl) tyramine ($C_{12}$) at concentrations ranging from 0.1 nM to 1 μM. Estrone sulfatase activity was determined from the amount of $^3H$-$E_1$ tritiated estrone and $^3H$-$E_2$ triated estradiol formed. The apparent I.C. 50 for the non-steroidal N-lauroyl-(p-o-sulfamoyl) tyramine ($C_{12}$) compound is between 1 and 2 nM. This is the concentration of the inhibitor to inhibit 50% of the sulfatase activity in the MDA-MB-231 cells.

Figure 4A:
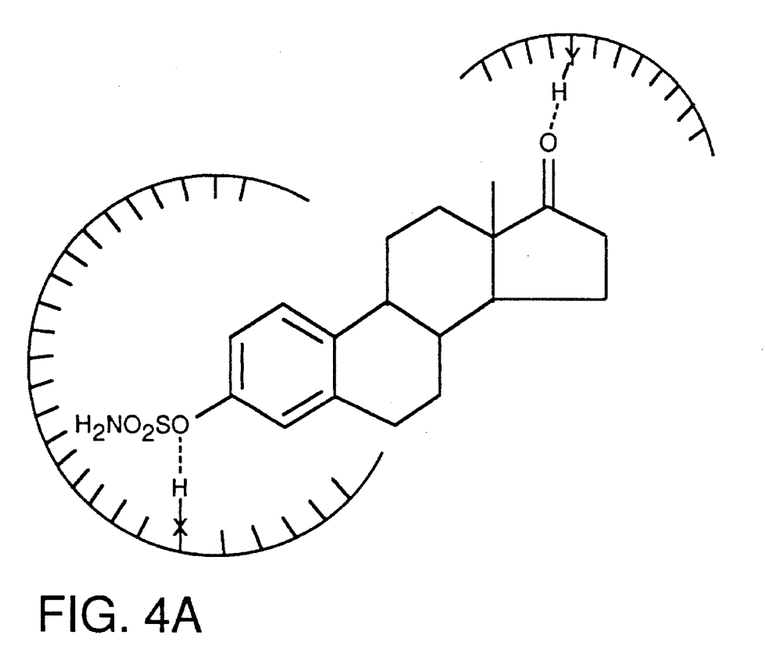
FIG. 4 discloses the interaction of both the steroidal sulfatase inhibitor and non-steroidal sulfatase inhibitor at the active site of the estrone sulfatase enzyme.
Figure 4B:
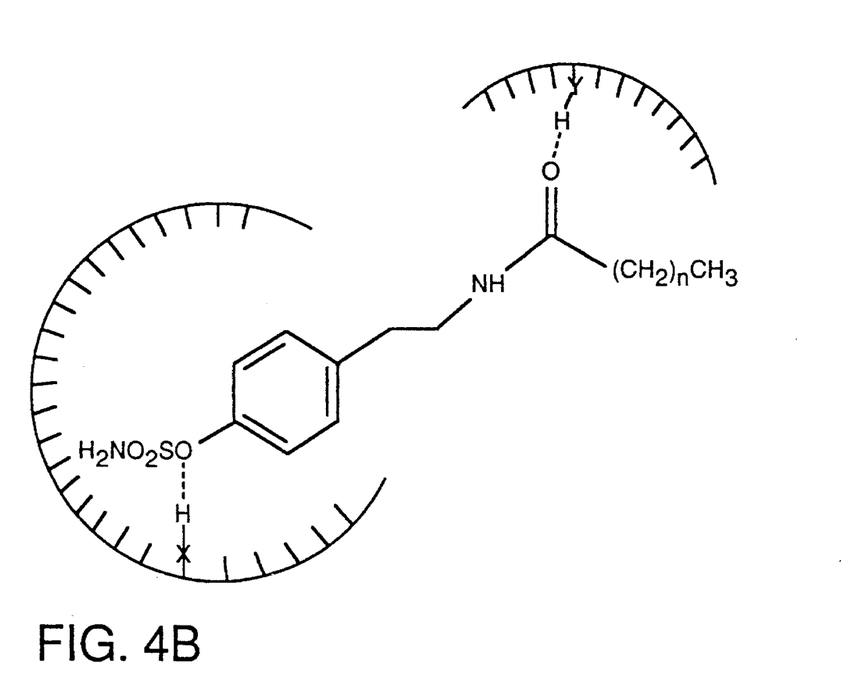
Figure 5:
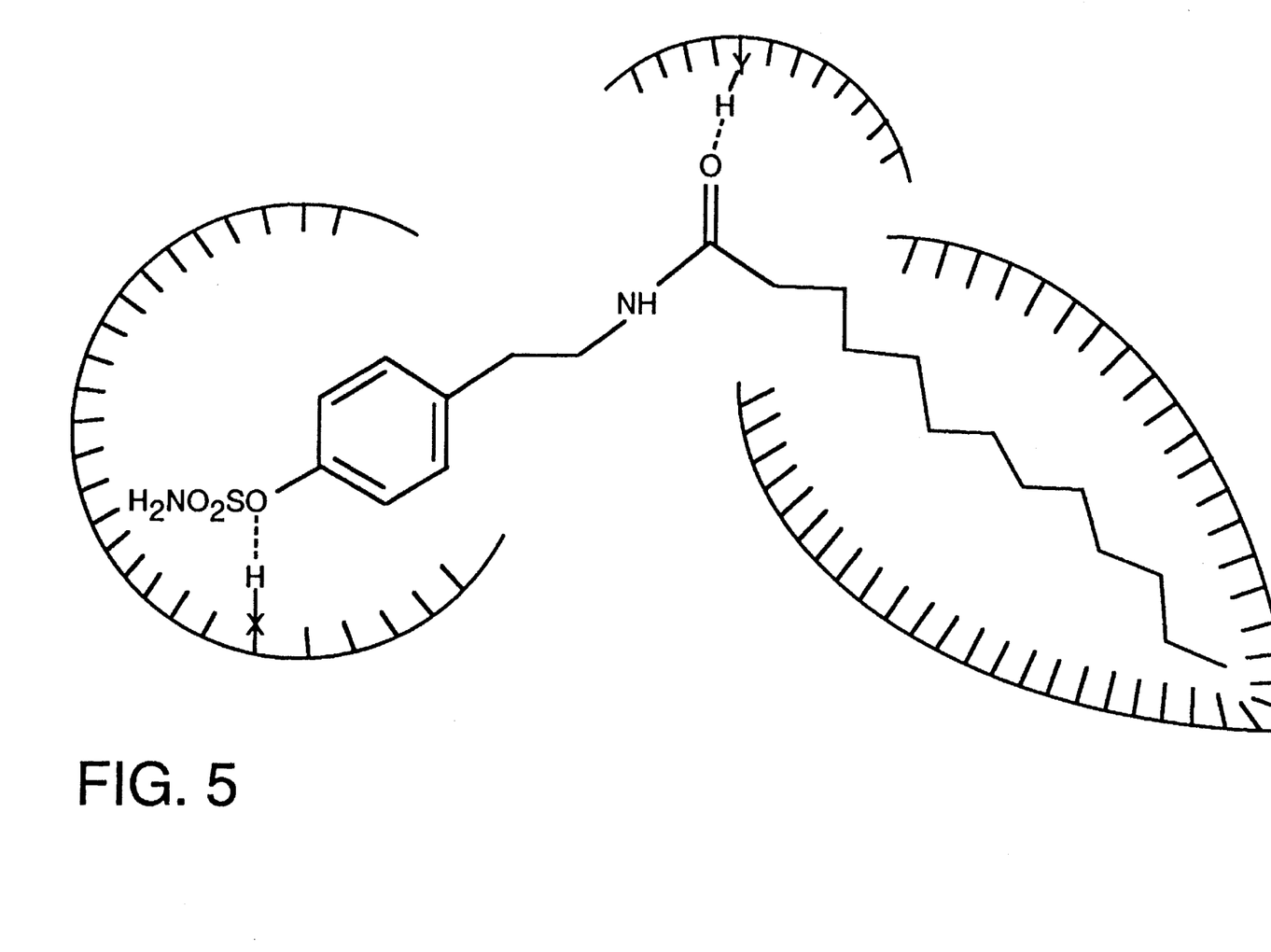
FIG. 5 shows a new binding characteristic of the non-steroidal inhibitors to the active site of the enzyme estrone sulfatase.

The designed non-steroidal inhibitors show potent sulfatase inhibitory activity when used with human term placenta. As the length of the alkyl chain increases from n=5 to 11, the inhibitory activity of the non-steroidal inhibitors increases by over 200 times. FIG. 4a illustrates the binding of the most potent sulfatase inhibitor, estrone sulfamate, with the active site of the enzyme sulfatase. There are two binding sites where enzyme (a) the aromatic A ring and the (b) 17-keto group. The non-steroidal sulfatase inhibitors (4b) of the present invention where n=5–14 has the same mode and efficiency of binding as the steroidal inhibitor estrone sulfamate shown in 4a. A new binding characteristic of the non-steroidal inhibitors to the active site of the enzyme estrone sulfatase is shown in FIG. 5. A third binding site at the active site of the enzyme is responsible for interacting with the alkyl side chain of the non-steroidal inhibitor and results in high binding affinity for the non-steroidal to the enzyme sulfatase.

Whereas particular embodiments of the present invention have been described above for purposes of the illustration, it will be evident to those skilled in the art that numerous variations of the details may be made without departing from the invention as defined in the appended claims.

I claim:

1. A compound comprising the formula (1)

wherein (a) $R_1$ is selected from the group consisting of hydrogen and a lower alkyl group, (b) $R_2$ is selected from the group consisting of H and a lower alkyl group, (c) m is an integer from 0 to 4, and (d) n is an integer from 5 to 14.

2. The compound of claim 1, wherein
   said lower alkyl group has 1 to 6 carbon atoms branched and unbranched.
3. The compound of claim 2, wherein
   $R_1$ is H, $R_2$ is H, m is 2 and n is 11.
4. The compound of claim 2, wherein
   $R_1$ is H, $R_2$ is H, m is 2 and n is 10.
5. The compound of claim 2, wherein
   $R_1$ is H, $R_2$ is H, m is 0 and n is 13.
6. A method of therapeutically treating a patient for estrogen dependent diseases comprising employing a compound having the formula (1)

wherein (a) $R_1$ is selected from the group consisting of hydrogen and a lower alkyl group, (b) $R_2$ is selected from the group consisting of H and a lower alkyl group, (c) m is an integer from 0 to 4, and (d) n is an integer from 5 to 14;
   incorporating said compound in a suitable pharmaceutical carrier;
   administering a therapeutically effective dosage of said compound incorporated in said carrier to said patient; and
   employing said method in therapeutically treating a patient for estrogen dependent diseases selected from the group consisting of breast cancer, ovarian cancer, vaginal cancer, endometrial cancer and endometriosis.
7. The method of claim 6, including
   employing as said carrier a solution selected from the group consisting of physiologic saline and 5% dextrose.
8. The method of claim 7, including administering said compound incorporated in said carrier to a patient by the parenteral route.
9. The method of claim 7, including
   administering said compound incorporated in said carrier to a patient by injection.
10. The method of claim 7, including
    administering said compound incorporated in said carrier to a patient by the oral route.
11. A method of prophylactically administering to a patient to provide protection as an estrogen depleting agent a compound having the formula (1)

wherein (a) $R_1$ is selected from the group consisting of hydrogen and a lower alkyl group, (b) $R_2$ is selected from the group consisting of hydrogen and a lower alkyl group, (c) m is an integer from 0 to 4, and (d) n is an integer from 5 to 11;
   incorporating said compound in a suitable pharmaceutical carrier;
   administering a prophylactically effective dosage of said compound incorporated in said carrier to a patient;
   employing said method in prophylactically administering to a patient to provide protection as an estrogen depleting agent against an estrogen dependent illness selected from the group consisting of breast cancer, ovarian cancer, vaginal cancer, endometrial cancer and endometriosis.
12. The method of claim 11, including
    employing as said carrier a solution selected from the group consisting of physiologic saline and 5% dextrose in water.

13. The method of claim 12, including
administering said compound incorporated in said carrier to a patient by the parenteral route.

14. The method of claim 12, including
administering said compound incorporated in said carrier to a patient by the oral route.

15. The method of claim 12, including
administering said compound incorporated in said carrier by injection.

16. A method for preparing the compound comprising the formula (1)

wherein $R_1$ is selected from the group consisting of hydrogen and a lower alkyl group, $R_2$ is selected from the group consisting of H and a lower alkyl group, m is an integer from 0 to 4 and n is an integer from 5 to 14, the method comprising:

adding alkanoyl chloride dropwise into a cooled solution of p-hydroxyphenylamine and triethylamine to form a first mixture;

extracting said first mixture to give a first product N-alkanoyl-p-hydroxyphenylamine;

adding a hydride and a sulfamide to said first product to form a second mixture;

extracting said second mixture to give a second product (p-o-sulfamoyl)-N-alkanoyl p-hydroxyphenylamine.

17. The method of claim 16, further including
stirring said first mixture at room temperature and pouring into acidic solution;

separating, drying, and concentrating under reduced pressure said first mixture to give said first product;

stirring said second mixture at room temperature and pouring into basic solution;

separating, drying and concentrating said second mixture under reduced pressure to give said second product.

18. The method of claim 17, including
employing HCl in said first mixture and extracting said first product with ethylacetate.

19. The method of claim 18, including
employing sodium bicarbonate in said second mixture and extracting said second product with methylene chloride.

20. The method of claim 19, wherein
the alkanoyl chloride has the formula (2)

wherein n is an integer from 5 to 14.

* * * * *